United States Patent
Paivarinta

[11] Patent Number: 5,289,592
[45] Date of Patent: Mar. 1, 1994

[54] EYE GLASS HOLDER

[76] Inventor: Reijo J. Paivarinta, #710-522 Moberly Rd., Vancouver, B.C., Canada, V5Z 4G4

[21] Appl. No.: 863,707

[22] Filed: Apr. 3, 1992

[51] Int. Cl.⁵ .................... A61F 9/02; A41D 21/00
[52] U.S. Cl. ............................. 2/431; 2/448; 2/453; 351/119; 351/120; 351/155
[58] Field of Search .................. 2/431, 10, 13, 453, 2/448, 209; 351/118, 120, 119, 155, 156, 158, 111; 379/430

[56] References Cited

U.S. PATENT DOCUMENTS

| | | | |
|---|---|---|---|
| 264,574 | 9/1882 | Shone | 351/119 X |
| 857,838 | 6/1907 | Shaw | 351/155 |
| 1,615,028 | 1/1927 | Morser. | |
| 2,443,249 | 6/1948 | Jackson | 351/118 X |
| 2,887,929 | 5/1959 | Farmer | 351/118 X |
| 2,989,598 | 6/1961 | Touger. | |
| 3,231,688 | 1/1966 | Ugartechea. | |
| 3,666,898 | 5/1972 | Ferrara. | |
| 3,841,741 | 10/1974 | Visher, Jr. | 351/120 |
| 3,907,410 | 9/1975 | Richmond | 351/119 |
| 3,938,614 | 2/1976 | Ahs | 2/209 X |
| 4,017,165 | 4/1977 | Davis | 351/120 |
| 4,129,362 | 12/1978 | Lorenzo | 351/123 |
| 4,367,929 | 1/1983 | Fortini | 351/119 |
| 4,544,245 | 10/1985 | Stansbury | 351/120 |
| 4,682,374 | 7/1987 | Geiser | 2/209 |
| 4,781,451 | 11/1988 | McAllen | 351/155 X |
| 4,864,611 | 9/1989 | Helmuth | 379/444 |
| 5,080,476 | 1/1992 | Monin | 351/119 |
| 5,092,667 | 3/1992 | Bagley | 351/156 |
| 5,133,596 | 7/1992 | Korny et al. | 351/158 |

FOREIGN PATENT DOCUMENTS

| | | | |
|---|---|---|---|
| 2708063 | 8/1977 | Fed. Rep. of Germany | 2/209 |
| 1552667 | 11/1968 | France | 351/120 |
| WO91/14195 | 9/1991 | PCT Int'l Appl. | 2/209 |

Primary Examiner—Peter Nerbun
Attorney, Agent, or Firm—Cahill, Sutton & Thomas

[57] ABSTRACT

A safety glass or spectacle assembly for use with a pair of ear defenders having a pair of lobes for sealing engagement with ears of a user. The assembly includes a safety glass or spectacle frame, an elongated set of arms each attachable to sides of the frame; and means for affixing ends of said arms remote from said frame to an exterior surface of respective lobes of the ear defender. By utilizing the exterior surface of the ear defender to attach the arms of the spectacles one avoids disrupting the seal of the lobes to the ears that are caused by using conventional safety glasses or spectacles.

12 Claims, 3 Drawing Sheets

EYE GLASS HOLDER

FIELD

The present invention relates to an eye glass holder for use in affixing eye glasses to a ear defender and permitting adjustment of the glasses to fit a user.

BACKGROUND

In an industrial or other work environment where noise is a problem it is common to provide workers with a pair of ear defenders which consist of large sound dampening ear pieces supported from the top of the head by a strap. If a user of such a device wears glasses or wishes to wear safety glasses then the only option is to break the seal of the ear pieces around the ear and insert the stems of the glasses over the user's ear, thereby offsetting the beneficial effects of the ear defenders. One of the problems in attaching safety glasses or any other glasses for that matter to a pair of ear defenders is the variability of positioning relative to the eyes of different users. Adjustments to both the length and the vertical positioning are required to properly position the lenses.

U.S. Pat. No. 264,574 issued to Shone discloses a set of spectacles mounted on the underside of a hat rim and suspended from hooks. Other than moving the hooks there is no adjustment shown. U.S. Pat. No. 4,129,362 issued to Lorenzo discloses an eyeglass structure having a pivot connection on the temple pieces proximate the ears and a tilt adjustment of the lenses by a pivotal keeper and a notched region on the temple arm for engagement by the keeper. There is nothing to restrain the temple arm portion from pivoting except apparently friction. Moreover, the course tilting adjustment is accomplished by a pawl which is not biased into engagement with the notched region. Consequently, it is not known how the pawl can stay reliably engaged with the notched region. In any event tilting adjustments done close to the lenses change the angle of the shield or glass significantly unlike such adjustments done further back along the temple arms.

Accordingly, it is an object of the invention to provide a set of eyeglasses or safety glasses which are capable of being mounted on a pair of ear defenders. A further object is to provide a set of such glasses which are adjustable not only in distance away from a face of a user but also in vertical position.

SUMMARY OF THE INVENTION

According to the invention there is provided a safety glass or spectacle assembly for use with a pair of ear defenders having a pair of lobes for sealing engagement with ears of a user. The assembly includes a safety glass or spectacle frame, an elongated set of arms each having one end attachable to a side of the frame, a swivel assembly, and means for affixing ends of said arms remote from said frame to an exterior surface of respective lobes of the ear defender. The arms can be pivoted about the swivel assembly to provide vertical pivoting of the frame about an axis proximate the ear defenders. By utilizing the exterior surface of the ear defender to attach the arms of the spectacles one avoids disrupting the seal of the lobes to the ears that are caused by using conventional safety glasses or spectacles.

Preferably, the affixing means includes a fastener strip on the lobes and mating fastener strips on the remote ends of the arms.

Advantageously, the arms may include a pair of ratchet swivel holders affixable to respective ones of the ear defender lobes and a pair of swivel arms connectable to each of the swivel holders such that the swivel arm is pivotal with respect to the holder at a point proximate an associated one of the lobes and is held in position after pivoting.

Preferably, the swivel arm assembly includes a swivel arm pivotally connectable to a corresponding one of said swivel holders and an arm support coupled to the spectacles or eye shield and removably attachable to the swivel arm.

Advantageously, in each of the swivel arm assemblies one of the arm support and said swivel arm has a serrated surface and another of the arm support and swivel arm has a pawl arm and a tooth at a distal end thereof which engages the serrated surface when the arm support and swivel arm are coupled together so as to allow longitudinal adjustment of the swivel arm and support arm relative to one another.

In each set of associated ratchet swivel holders and swivel arms one of the ratchet swivel holder and swivel arm includes a pair of spaced apart discs with axially aligned holes therein and a serrated partial cylindrical surface therebetween while another of the ratchet swivel holder and swivel arm includes a ratcheting disc at an end thereof identical in radius to the pair of discs and has a pair of axial aligned shaft portions which slidably fit into the aligned holes in the pair of discs. The ratcheting disc may have a tooth projecting outwardly therefrom mounted on a radially movable flexible mounting such that the tooth is normally in engagement with the serrated surface and but is movable thereover in response to torque applied to the swivel holder relative to the support arm.

Each of the swivel arms may have an elongated rectangular arm support receptacle, a pawl arm, and a tooth on an end of the pawl arm projecting inwardly of the receptacle. Each of the support arms may be dimensioned to slide into the arm support receptacle and may have a notched region on one surface thereof which is engaged by the tooth.

The radially movable flexible mounting on the ratcheting disc may include a slot in the disc directed parallel to an axis of the disc which runs radially proximate a periphery thereof and opens to the periphery adjacent the tooth so as to form a cantilevered arm with the tooth at a distal end thereof.

By providing for pivoting of the swivel arm assembly remote from the spectacles near the ear defender lobes the lenses or shield does not change angle appreciably on adjustment. Length adjustment of the arms allows placement of the lense at a desired position away from the face and eyes. Use of a ratcheting action permits a secure positioning without moving any locking arms, pins or other mechanisms once the adjustments have been made.

By providing support arms which can easily be removed from respective swivel arms and by permanently attaching the swivel holders to the ear defender lobes as, for example, by epoxy, the theft of the spectacles or safety glasses is unattractive as the glasses are unusable without the remainder of the assembly.

BRIEF DESCRIPTION OF THE DRAWINGS

The novel features believed to characterize the invention are set forth in the appended claims. The invention itself, however, as well as other features and advantages thereof, will be best understood by reference to the detailed description which follows, read in conjunction with the accompanying drawings, wherein:

DETAILED DESCRIPTION WITH REFERENCE TO THE DRAWINGS

Figure 1:
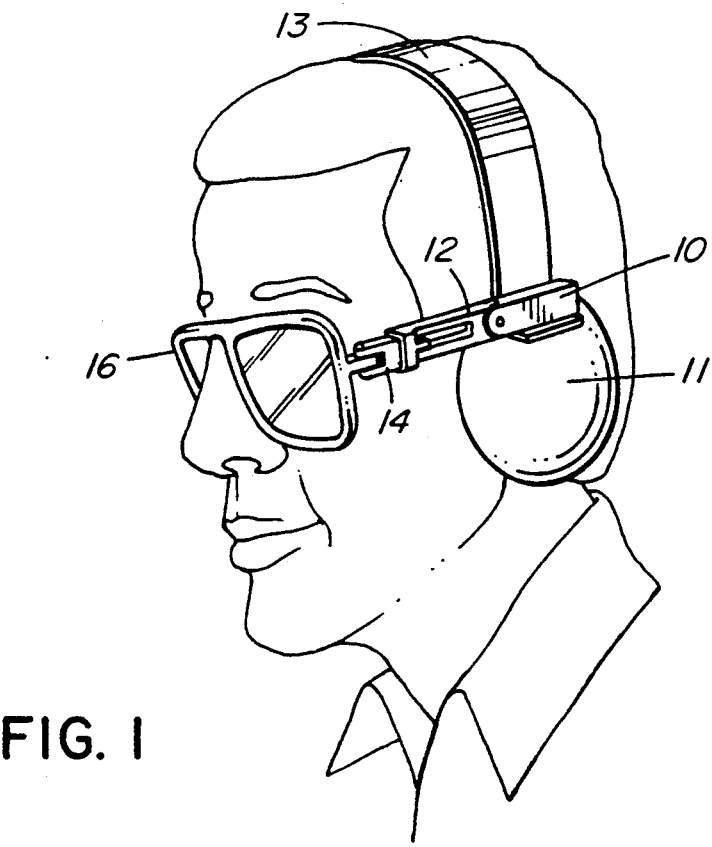
FIG. 1 is a side elevation view of a user with a pair of ear defenders and a pair of glasses in accordance with a preferred embodiment of the present invention attached to the ear defenders.
Figure 2:
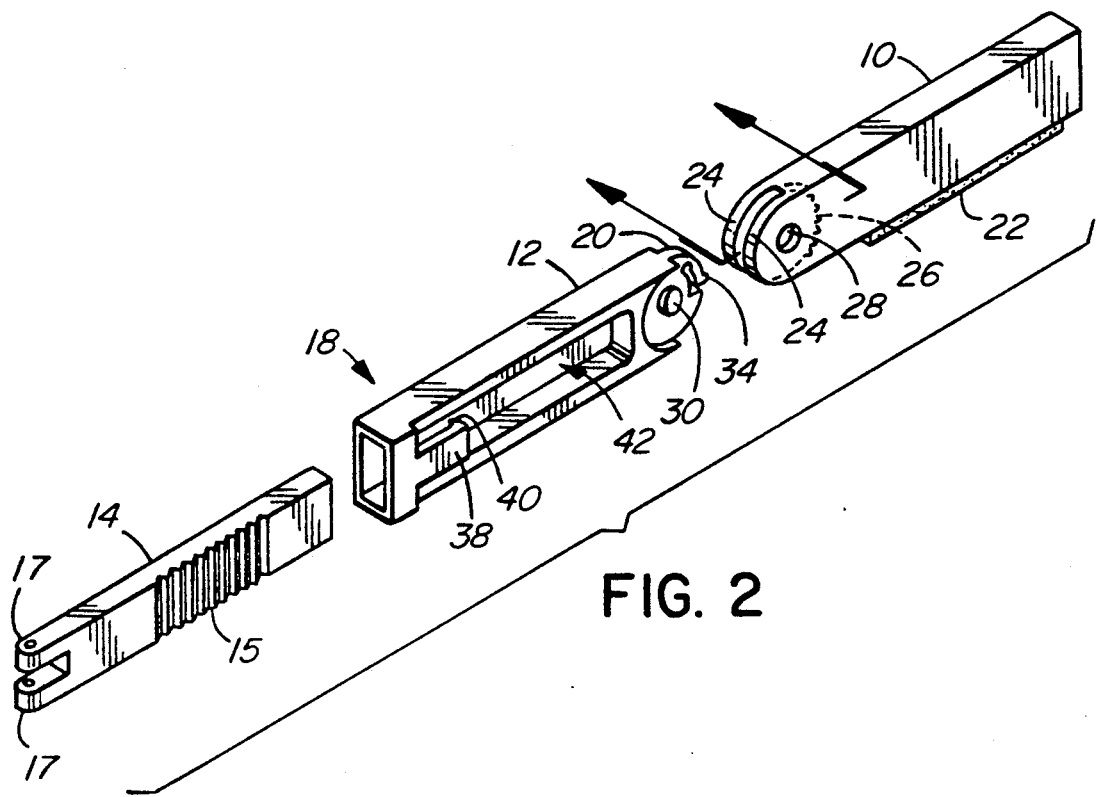
FIG. 2 is an exploded perspective view of one of the temple arm assemblies and retainer arms without a lens attached.

Referring to FIG. 1 a pair of spectacles 16 which could be either ordinary glasses, safety glasses or sun glasses are connected by standard hinges to respective temple arm assemblies 18. Each temple arm assembly 18 includes an arm support 14 and a swivel arm 12 having an arm receptacle 42 (see FIGS. 2 to 6) into which the arm support 14 is insertable. Each swivel arm 12 is pivotally coupled to a ratchet swivel holder 10 and the latter is attached to an upper portion of an ear defender lobe 11.

Figure 3:
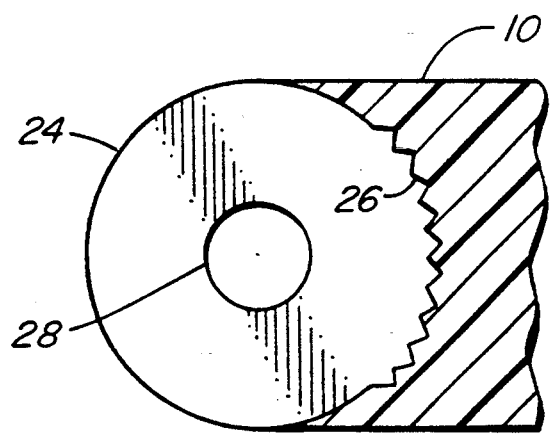
FIG. 3 is a partial sectional view taken along the line 3—3 of FIG. 1.

Referring to FIGS. 2 to 6 it will be understood that there are two temple arm assemblies 18 which are identical. In the following discussion the components of each temple arm assembly will be referred to in the singular for convenience. The ratchet swivel holder 10 has a fastener strip affixed to its underside which removably engages with a corresponding receiving strip affixed onto the top of it associated ear defender lobe 11. The end of the holder 10 is rounded with two spaced apart circular discs 24 each having axial swivel holes 28 with the discs being integral with the rest of swivel holder 10. In the region between the two discs 24, the surface of holder 10 is formed into a serrated circular surface 26 as shown in FIG. 3.

Figure 4:
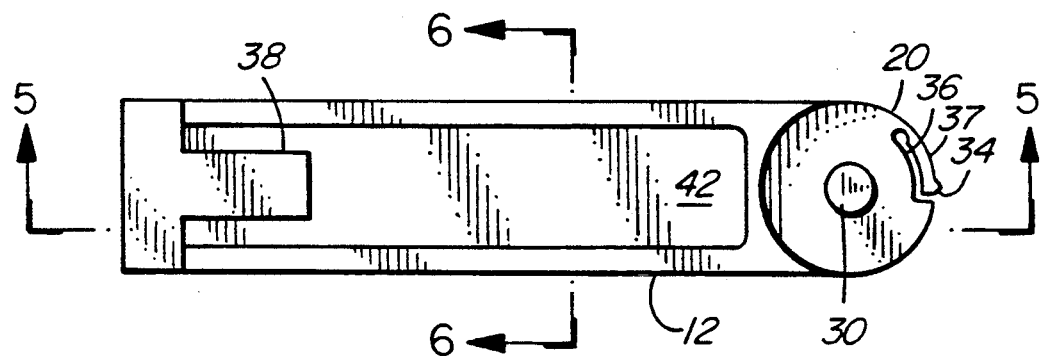
FIG. 4 is a side elevation view of the swivel arm.
Figure 5:
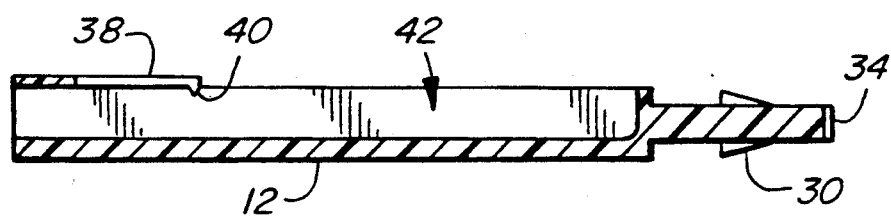
FIG. 5 is a sectional view along the line 5—5 of FIG. 4.
Figure 6:
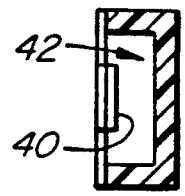
FIG. 6 is a sectional view along the line 6—6 of FIG. 6.

Swivel arm 12 has formed at its end a disc 20 having a pair of opposed inclined shaft portions 30 dimensioned to snap into swivel holes 28 upon insertion of disc 20 between discs 24. As seen in FIG. 4, at the periphery of disc 20 there is formed an outwardly projecting tooth 34. Adjacent tooth 34 there is a swivel tooth slot 36 which runs radially around the disc 20 near the periphery thereof to form a flexible arcuate lever 37. When disc 20 is inserted between discs 24, tooth 34 engages serrated surface 26 to hold swivel arm 12 in place. Torque applied to swivel arm 12 causes flexible arm 37 to bend and tooth 34 to move over serrated surface 26, thereby allowing arm 12 to pivot.

Arm 12 has an arm support receptacle 42 open at an end opposite disc 20. A pawl arm 38 with an inwardly projecting tooth 40 is formed over receptacle 42. Arm support 14 is dimensioned to slide along receptacle 42. On one surface of arm support 14 there is formed a notched or serrated surface 15. At an end of the arm 14 there are two hinge plates 17 which are pinned to a plate that fits between plates 17 and are pinned so as to be able to pivot laterally. When arm 14 is inserted into receptacle 42, tooth 40 engages notched surface 15 to hold it against movement along the length thereof. The notched surface allows for a length adjustment of approximately one inch.

In use the ratchet swivel holder 10s are first mounted by placing their Velcro strip 22 in contact with the corresponding mating Velcro strip on the top of the ear defender lobes 11 with the discs 24 in a forward direction. Next swivel arm 12 is coupled to ratchet swivel holder 10 as explained above. Finally the spectacles 16 which are hingedly attached to arm supports 14 are coupled to the swivel arms 12 by inserting them into arm support receptacles 42 and moving them to the correct position so that the spectacles are an acceptable distance from the face of a user. Next swivel arm 12 and arm support 14 are pivoted by rotating disc 20 relative to discs 24 until the spectacles are off of the nose of a user at a desired elevation. It is also possible to pivot the glasses upwardly out of the way by moving tooth 34 over serrated surface 26 until it reaches the bottom of the latter.

Figure 7:
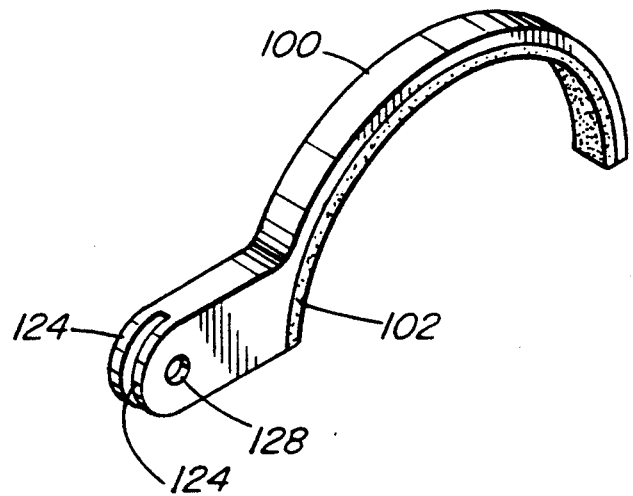
FIG. 7 is a perspective view of a swivel arm holder of an alternative shape.

A swivel arm holder 100 having an alternative shape is seen in FIG. 7 in which the portion which engages the lobe of the ear defender is shaped to conform to the shape of the top of the lobe. Fastener strip 2 is one of a male and female type of removable interconnecting fasteners sold under the trademark Velcro. In this case the larger area of attachment coupled with the larger counterbalancing lever arm provided by the semicircular lobe contact region enhances the resistance to removal. Discs 124 and hole 128 are identical to discs 24 and hole 28 in FIG. 2.

Clearly it would be possible to reverse arm support 14 and swivel arm 12 by making arm 12 insertable into arm support 14. Similarly, it would be possible to make the serrated surface 26 on swivel arm 12 and the tooth 34 on arm 10. Moreover, it is obvious that other methods of attachment of retainer arm 10 to lobe 11 are possible such as gluing the two together, screwing the two together etc.

It is also clear that some flexibility in the materials of arms 10 and 12 is desirable as would be provided by, for example, a plastic material.

It will be appreciated that the only portion of the temple assemblies which are designed to be removed from the ear defender is spectacles 16 and arm supports 14 should ratchet swivel holder 10 be permanently fastened to lobe 11. In such a case there would be no incentive for a person to steal the glasses as he or she would not be able to use them without the remainder of the temple assemblies.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modification or embodiments as fall within the true scope of the invention.

I claim:

1. A safety glass or spectacle assembly for use with a pair of ear defenders having a pair of lobes for sealing engagement with ears of a user, comprising:
   (a) a safety glass or spectacle frame;
   (b) an elongated set of arms each attachable to sides of said frame and each arm having a ratchet swivel assembly positioned remotely from said frame; and
   (c) means for affixing ends of said arms remote from said frame to respective lobes of said ear defender;
   wherein said arms can be pivoted about said ratchet swivel assembly to provide vertical pivoting of said frame about an axis remote from said frame.

2. An assembly according to claim 1, wherein said affixing means includes fastener strips on the remote ends of said arms.

3. A safety glass or spectacle assembly for use with a pair of ear defenders having a pair of lobes for sealing engagement with ears of a user, said assembly comprising:
   (a) a pair of swivel holders having means to affix onto respective ear defender lobes;
   (b) a ratchet swivel arm assembly connectable to each of said swivel holders in engagement therewith such that said swivel arm assembly is pivotal with respect to said holder at a point remote from a spectacle or eye shield frame and is held in position after pivoting; and
   (c) a set of spectacles or an eye shield attachable to said swivel arm assemblies.

4. An assembly according to claim 3, wherein said ratchet swivel arm assembly includes a swivel arm pivotally connectable to a corresponding one of said swivel holders and an arm support coupled to said spectacles or eye shield and removably attachable to said swivel arm.

5. An assembly according to claim 4, wherein in each of said swivel arm assemblies one of said arm support and said swivel arm has a serrated surface and another of said arm support and swivel arm has a pawl arm and a tooth at a distal end thereof which engages the serrated surface when said arm support and swivel arm are coupled together so as to allow longitudinal adjustment of the swivel arm and support arm relative to one another.

6. An assembly according to claim 3, wherein in each set of associated swivel holders and swivel arms one of said swivel holder and swivel arm includes a pair of spaced apart discs with axially aligned holes therein and a serrated partial cylindrical surface therebetween and another of said swivel holder and swivel arm includes a ratcheting disc at an end thereof identical in radius to said pair of discs and has a pair of axial aligned shaft portions which slidably fit into the aligned holes in the pair of discs and said ratcheting disc has a tooth projecting outwardly therefrom and is mounted on a radially movable flexible mounting, being normally in engagement with said serrated surface and movable thereover in response to torque applied to said swivel holder relative to said support arm.

7. An assembly according to claim 5, wherein each of said swivel arms has an elongated rectangular arm support receptacle, a pawl arm, and a tooth on an end of said pawl arm projecting inwardly of said receptacle, and each of said support arms is dimensioned to slide into said arm support receptacle and has a notched region on one surface thereof which is engaged by said tooth.

8. An assembly according to claim 6, wherein said radially movable flexible mounting on said ratcheting disc includes a slot in said disc directed parallel to an axis of said disc and running radially proximate a periphery thereof and opening to the periphery adjacent said tooth so as to form a cantilevered arm with said tooth at a distal end thereof.

9. A safety glass or spectacle assembly for use with a pair of ear defenders having a pair of lobes for sealing engagement with ears of a user, comprising:
   (a) a pair of ratchet swivel holders affixable to respective ear defender lobes, each of said holders having a pair of spaced apart discs and an arcuate surface therebetween, with each disc having an axially aligned shaft hole and the arcuate surface of said holder between said discs being serrated;
   (b) a swivel arm having a disc dimensioned to fit between said ratchet swivel holder discs, shaft portions located centrally on either side of said disc which fit into and rotate in said shaft holes;
   (c) a flexible, cantilevered radial lever formed around a periphery of said swivel arm disc and an outwardly projecting tooth at a distal end of said lever engaging the serrated surface;
   (d) a support arm slidably engageable with said swivel arm;
   (e) means for providing friction between said support arm and said swivel arm; and
   (f) a set of spectacles attachable to said support arm.

10. An assembly according to claim 9, wherein one of said support arm and said swivel arm has an elongated receptacle and the other is slidably insertable into said receptacle.

11. An assembly according to claim 9, wherein said swivel arm has an elongated support arm receptacle and said support arm is slidably insertable therein.

12. An assembly according to claim 11, wherein said friction providing means includes a serrated surface on said support arm and a pawl coupled to said swivel arm and having a tooth at a distal end thereof projecting inwardly and engaging said serrated surface.

* * * * *